United States Patent [19]
Grendahl et al.

[11] Patent Number: 4,661,108
[45] Date of Patent: Apr. 28, 1987

[54] INTRAOCULAR LENS

[75] Inventors: Dennis T. Grendahl, Excelsior, Minn.; William LeMaster, Goleta, Calif.

[73] Assignee: Surgidev Corporation, Goleta, Calif.

[21] Appl. No.: 751,555

[22] Filed: Jul. 3, 1985

[51] Int. Cl.⁴ .............................................. A61F 2/16
[52] U.S. Cl. ........................................................ 623/6
[58] Field of Search ........................................... 623/6

[56] References Cited

U.S. PATENT DOCUMENTS

| Re. 31,626 | 7/1984 | Hoffer | 623/6 |
| Re. 31,998 | 10/1985 | Myers | 623/6 |
| 4,168,547 | 9/1979 | Konstantinov et al. | 623/6 |
| 4,244,060 | 1/1981 | Hoffer | 623/6 |
| 4,412,359 | 11/1983 | Myers | 623/6 |

OTHER PUBLICATIONS

The Hoffer Ridge Lenses from Cilco (Advertisement Brochure), Cilco, Inc., 6 pages, Mar. 1983, 623-6.
New Nova Aid Kratz Elliptical Posterior Chamber Lens, Model 822, Advertisement frm Cooper Vision IOL, 3 pages, received in PTO Jul. 13, 1983, 623-6.

Primary Examiner—Ronald L. Frinks
Attorney, Agent, or Firm—Hugh D. Jaeger

[57] ABSTRACT

Intraocular lens including a meniscus lens optic with a convex anterior surface, a concave posterior surface and a double barrier ledge. The double barrier ledge includes an interrupting channel. A plurality of loops, such as continuously curved J-shaped blue loops, secure at an angle of 0°–10° to the plane of the optic. The double barrier ledge, including the U-shaped channel or other geometrically configured channel between the two ledges, provides a double barrier ledge like seal around the posterior capsule of the eye holding back migration of the cortical epithelium. The double barrier ledge causes a seal which prevents aqueous flowing back to the optical zone of the capsular bag. In the case of a dissection or laser capsulotomy, the double barrier seal prevents vitreous strands from passing beyond and inner edge of the ledge. Other optics for lenses, such as plano-convex or bi-convex, can utilize the double ledge principle.

11 Claims, 8 Drawing Figures

INTRAOCULAR LENS

BACKGROUND OF THE INVENTION

1. Field of the Invention

The present invention pertains to an intraocular lens, and more particularly, to a double barrier ledge IOL (intraocular lens).

2. Description of the Prior Art

The prior art meniscus lenses have failed to provide a double barrier ledge. The prior art lenses have only provided a single ledge which are less likely to provide for holding back of the cortical debris from the optical zone of the capsular bag and further may provide the possibility that vitreous strands can leak out around the optic. The lenses which have a laser meniscus space also have not provided a proper ledge like seal around the posterior capsule, and more importantly, have not produce a large enough space to preclude the possibility of the posterior capsule adherence to the lens optic.

Two representative prior art U.S. Patents are Hoffer, U.S. Pat. No. RE 31,6265, July 10, 1984, and Meyer U.S. Pat. No. 4,412,359, Nov. 1, 1983. The Hoffer patent does not provide a ledge, but discloses projections or lips of a spike configuration extending rearwardly from the lens body. The Meyers patent does not provide a channeled rear ledge, but provides an outer continuous rear edge which abuts against the posterior capsule.

The present invention overcomes the deficiencies of the prior art by providing a meniscus lens or any other type of lens optic with a double barrier ledge.

SUMMARY OF THE INVENTION

The general purpose of the present invention is to provide an intraocular lens with a double barrier ledge. Other types of lens optics can also be provided with a double barrier ledge. The dual barrier ledge provides a capture area with a relaxed transition space in between. The integrity of the double seal by the double ledge is not compressed allowing for contraction of the posterior surface. A multiple barrier channeled ledge extends about the optic surfaces and includes a plurality of downwardly extending ledges having a channel therebetween which extend in a posterior direction away from the posterior surface so as to space the posterior lens surface from the posterior capsule while forming a double seal therewith when engaged with the posterior capsule.

According to one embodiment of the present invention, there is provided a convex-concave meniscus optic with a concave posterior surface extending across the entire optic, the optic varying in power and including flexible blue PMMA loop material of finite length at a 0°-10° angulation for securing the lens in the posterior chamber. The lens includes an outwardly extending double barrier ledge with an interrupting channel therebetween. The lens can be made of PMMA, as well as the loops, polysulfone, or any other like material. The principle of the double barrier ledge is also applicable to other types of lenses. The optic can be plano-convex or any other suitable lens optic. The double barrier ledge can be about the optic surfaces providing for a number of configurations of not only a lens with a lower surface but also a lens with upper and lower ledges.

One significant aspect and feature of the present invention is an optic which includes a double barrier ledge, and does not reduce the optical significance and the usable optical zone. A nominal space allows for the YAG Laser Capsulotomy, and also puts the capsule in stretch. This reduces striae or wrinkling of the capsular bag. The ledge rear surface of the channeled rear ledge abuts against the posterior surface creating a barrier or seal between the lens and the capsular bag thereby preventing migration of the endothelial cells. The optic can be 6 mm-7 mm diameter by way of example. An outer edge is interrupted by the haptics.

Another significant aspect and feature of the present invention is a concave or plano posterior surface which extends across the entire optic, thereby providing a larger target area for YAG. The surgeon can create capsulotomies of greater diameter.

A further significant aspect and feature of the present invention is one smooth rearward surface eliminating posterior complications. The greater posterior surface area is for a contact zone by the ledge minimizing epithelial cell migration and penetration of the barrier zone created by the channeled interrupted rear ledge.

Having thus described one embodiment of the present invention, it is the principal object hereof to provide a meniscus lens with a nominal space between the center of the posterior surface of the lens and the posterior chamber capsule. The lens includes blue or clear loops, which may be made of PMMA, is of a finite thickness, and includes a double barrier ledge.

One object of the present invention is a meniscus lens with nominal spacing between the posterior wall of the capsule and the posterior wall of the optic providing a margin of safety so a surgeon does not pit the lens optic of the IOL during YAG Laser Capsulotomy.

Another object of the present invention is a meniscus lens with the double barrier ledge which provides an inherent seal, decreasing epithelium migration, as well as decreasing any likelihood of the leaking out of vitreous strands because of the amount of space between the "bag" and concave surface of the lens optic.

A further object of the present invention is a double or dual barrier ledge which is applicable to lenses utilized in YAG Laser Capsulotomies.

DESCRIPTION OF THE PREFERRED EMBODIMENTS

Figure 1:
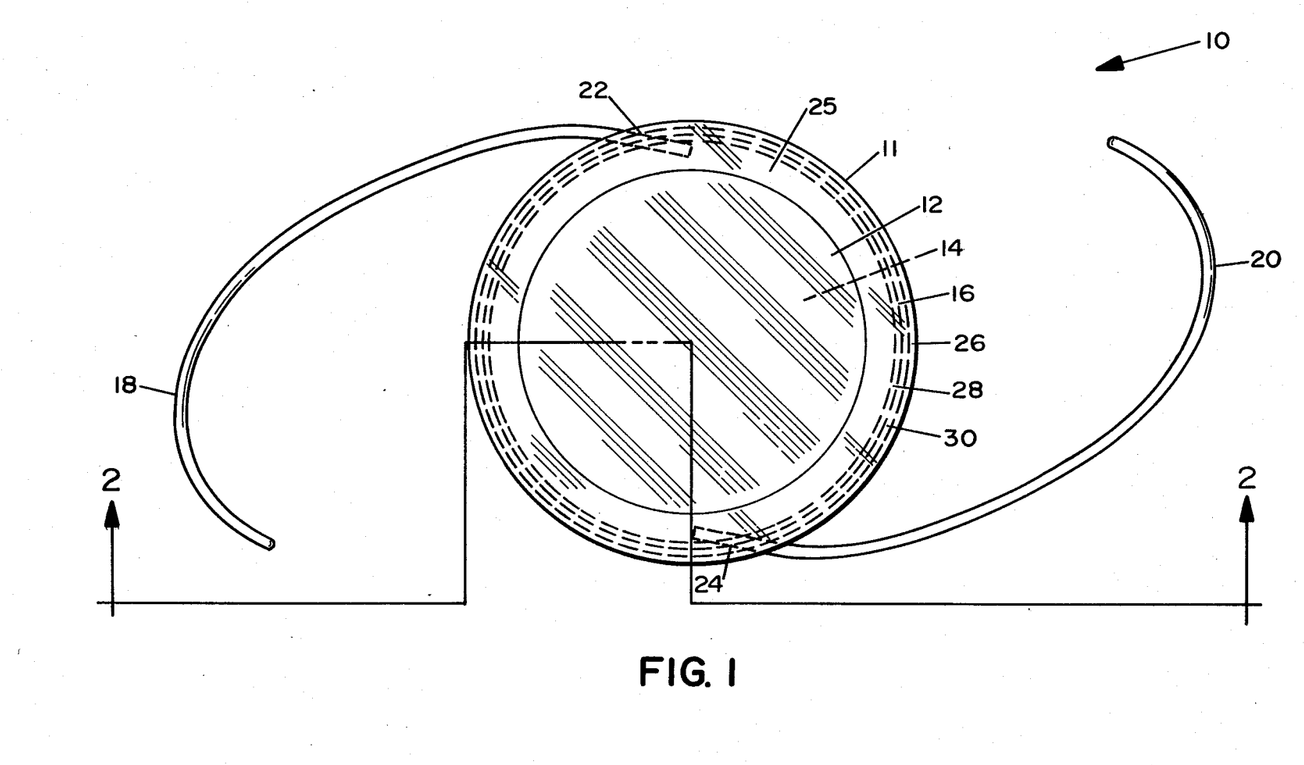
FIG. 1 illustrates a plan view of a lens.
Figure 2:
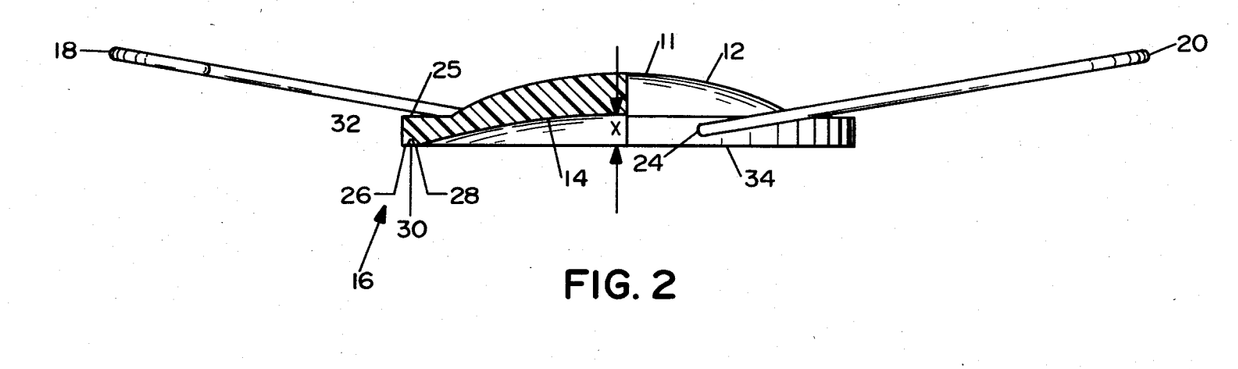
FIG. 2 illustrates a partial side view and a partial sectional view of FIG. 1.

FIG. 1 illustrates a plan view of an intraocular lens 10 including an optic 11 of PMMA material, an anterior convex surface 12, a posterior concave surface 14, and a double or dual barrier ledge 16 for the ledge lens, as also illustrated in FIG. 2. Two continuously curved J-shaped loops 18 and 20, of blue or clear PMMA material, secure into holes 22 and 24, respectively, by known processes. The continuously curved J-shaped loops may be angled at 10°, as illustrated in FIG. 2, although the loops can be C-shaped or J-shaped, or a combination of these loops or other loops and at an angle of 0°–10°. The distance, "x" in FIG. 2, between the concave surface to the bottom plane of the lens is nominal. This provides space for YAG Laser Capsulotomy. While the optic and loops can be of PMMA, any other suitable material, such as polysulfone or like material, can be utilized. The lens can also be made as a one-piece lens, such as a molded lens or lathe cut lens including haptics. The double barrier ledge 16 has an upper ledge or upper land surface 25, and lower ledges 26 and 28 of FIG. 2. A channel 30 is between the ledges 26 and 28, and can assume a geometrical configuration such as U-shape, wedge shaped, oval, elliptical, square, rectangular, or any other geometrical shape. The lens can include any plurality or multiple of lower ledges with alternating channels in between the ledges. This then provides a multiple barrier lens. While reference has been made to a double barrier lens, this is by way of example and for purposes of illustration only, and not to be construed as limiting of the present invention. The ledges of the optic can also assume a rounded configuration. Also, the lens optic can be a plano-convex, biconvex, or other lens optical configuration. An outer edge 32 surrounds the upper ledge 25 and lower ledges 26 and 28.

The optic 11 can be 7 mm in diameter where 6 mm is for the optical field and ½ mm on either side is for securing the haptics and positioning holes. This design, which can be termed as a "land" lens, "flying saucer" lens or "ledge" lens, minimizes bulk while providing an optimized optical field.

FIG. 2 illustrates a partial side view and a partial sectional view of the lens 10 of FIG. 1 where all numerals correspond to those elements previously described. The figure illustrates the particular angle and placement of the loops 18 and 20 with respect to the optic 11 where the loops insert into the ledges side edge member in holes 22 and 24, respectively, as illustrated also in FIG. 2. An "x" in between the arrows illustrates nominal spacing of preferably in the range of 0.3 mm between the posterior concave wall 14 of the optic 11 and a plane of the bottom of the optic 11. The loops are nominally at an angle of 10°, and in the range of 0°–10°. The double barrier ledge 16 includes dual ledge member 26 and 28, and a U-shaped or other like geometrical channel 30 forming the interrupted channeled double barrier ledge 16. The double barrier ledge 16 can also be referred to as a dual barrier ledge. The ledge or land 16 is offset from the lens optic 11 by the width of the dual barrier ledge and the channel in between, plus the width from the point where the anterior surface 12 ceases curvature to the beginning of the inner edge of the inner ledge member 28. The anterior surface 12 of the optic 11 is offset with respect to the posterior surface 14 of the optic also providing an increased optical area. A lower plane 34 is formed at the junction of the rear posterior surface 14 and the inner lower ledge 28. The upper ledge 25 is greater in planar length than the channeled interrupted lower ledges 26–30, although depending upon the optic curves, the upper ledge could be shorter in length than the channel interrupted lower ledges. The geometrical cross-section of the specific ledge surfaces and channel is best illustrated in FIG. 2.

MODE OF OPERATION

The meniscus lens is designed to provide a laser space between the lens and the posterior capsule with nominal space. This lens particularly lends itself to YAG Laser Capsulotomies which is becoming the treatment modality of choice for secondary opacification. This lens facilitates the opening of the capsule while still resisting YAG laser damage. The lens 10 creates a double barrier or dual barrier ledge 16 with a seal of 360° around the posterior capsule, which holds back migration of the cortical epithelium and still provides a proper gap between the center of the lens and the capsular bag. The PMMA loops 18 and 20 put the capsule in stretch which in turn allows the capsular bag to be opened with a lower YAG power setting and fewer shots. The meniscus lens is such that a large target area for the YAG Laser is provided. This lens provides a safe target area. The lens provides a margin of safety of the nominal spacing so that the surgeon hits the capsular bag with the YAG Laser, and not the IOL optic so as not to pit the lens optic. This spacing further precludes adherence of the posterior wall of the capsule to the posterior wall of the optic or "sucking up" of the wall of the capsule to the optic.

ALTERNATIVE EMBODIMENTS

Figure 3:
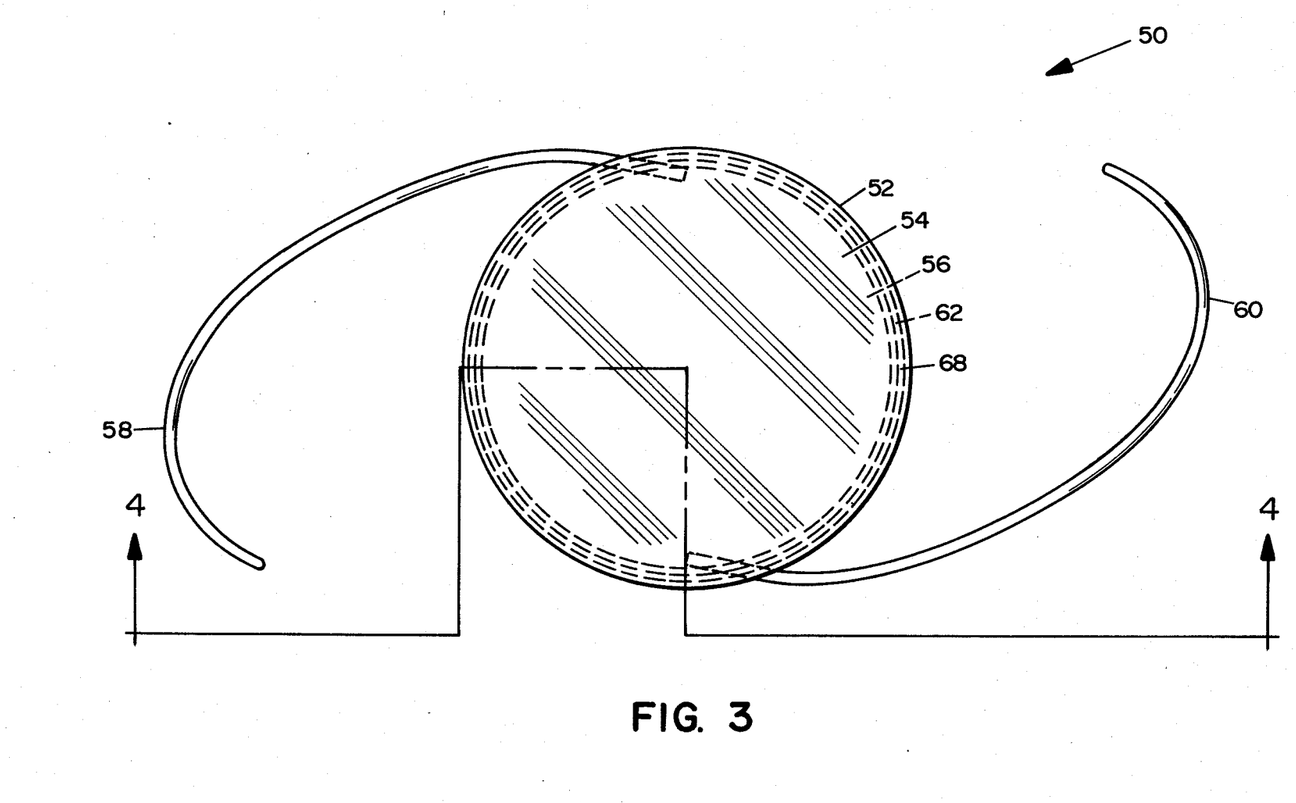
FIG. 3 illustrates a plan view of a lens.

FIG. 3 illustrates a plan view of an intraocular lens 50 including an optic 52 with a convex anterior surface 54 and a concave posterior surface 56. Two loops 58 and 60 secure to the edge of the optic as previously described in FIGS. 1 and 2. A double barrier ledge 62, as also illustrated in FIG. 4, including an inner ledge 64 and an outer ledge 66, separated by a channel 68, extend downwardly from the edge of the anterior surface 54.

Figure 4:
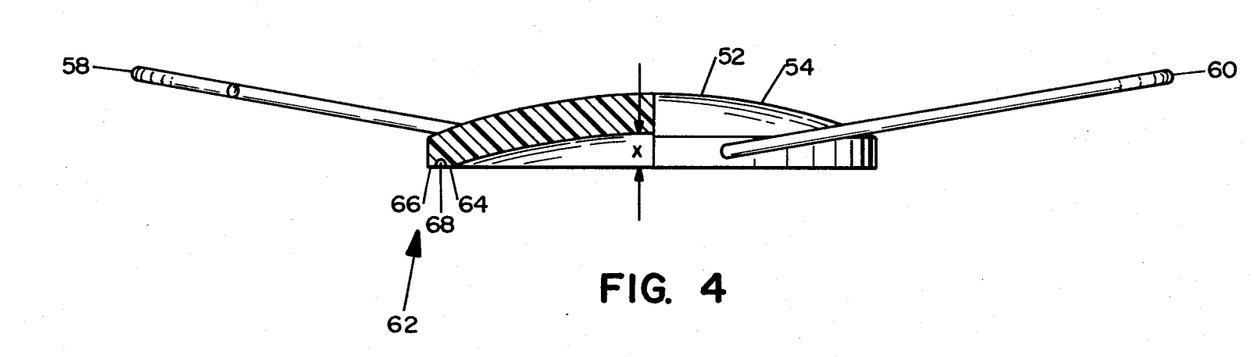
FIG. 4 illustrates a partial side view and a partial sectional view of FIG. 3.

FIG. 4 illustrates a partial side view and a partial sectional view of FIG. 3 where all numerals correspond to those elements previously described. It is illustrated that the outer edge of the outer ledge 66 is substantially in line with the edge of the optic surface 52 forming a smooth surface contrary to FIGS. 1 and 2 where the dual barrier ledge is offset outwardly past and beyond the point where the anterior surface of curvature ceases. The particular degree of offsetting of the dual barrier ledge can also vary between the examples of FIGS. 1 and 2 and FIGS. 3 and 4. An "x" in between the arrows illustrates nominal spacing of preferably 0.3 mm between the posterior concave wall 56 of the optic 52 and a plane of the bottom of the optic 52.

Figure 5:
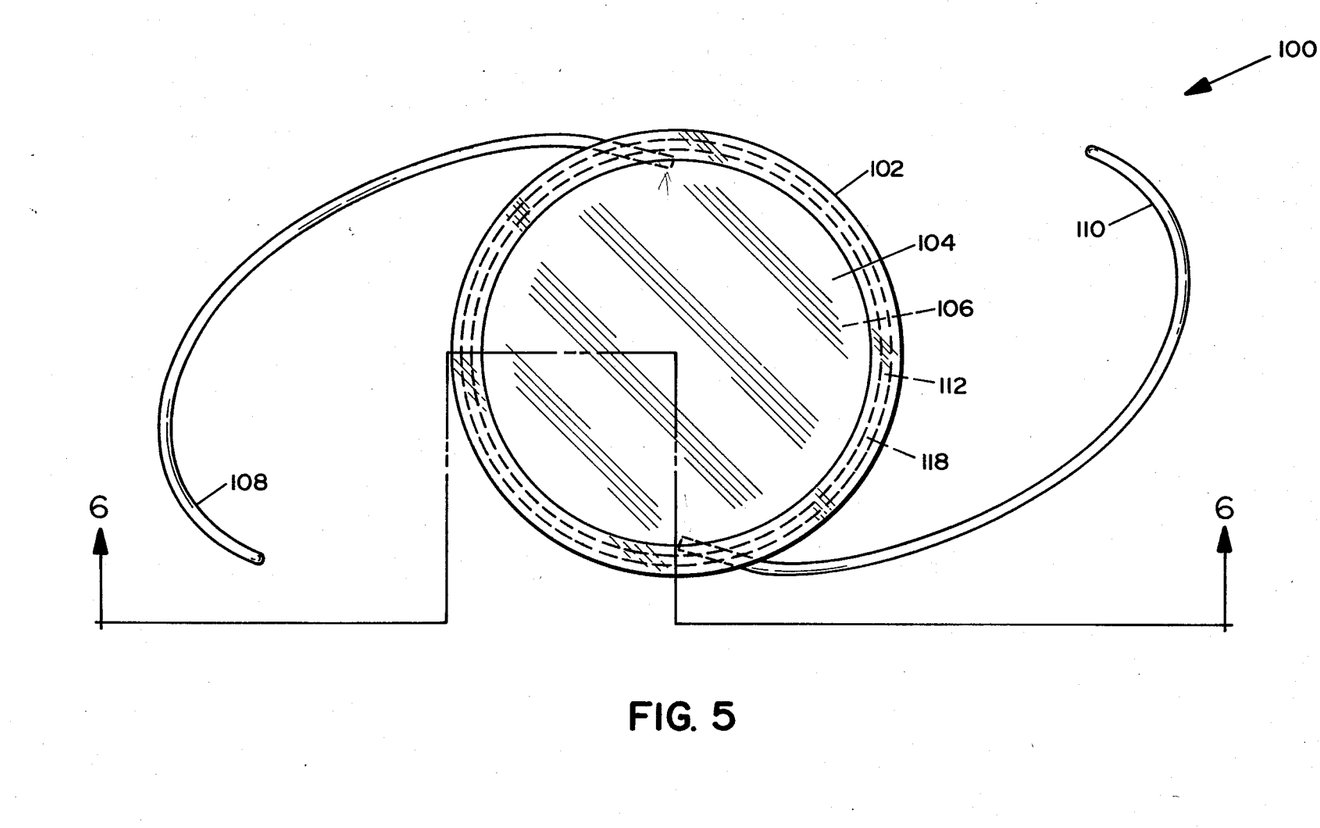
FIG. 5 illustrates a plan view of a lens.
Figure 6:
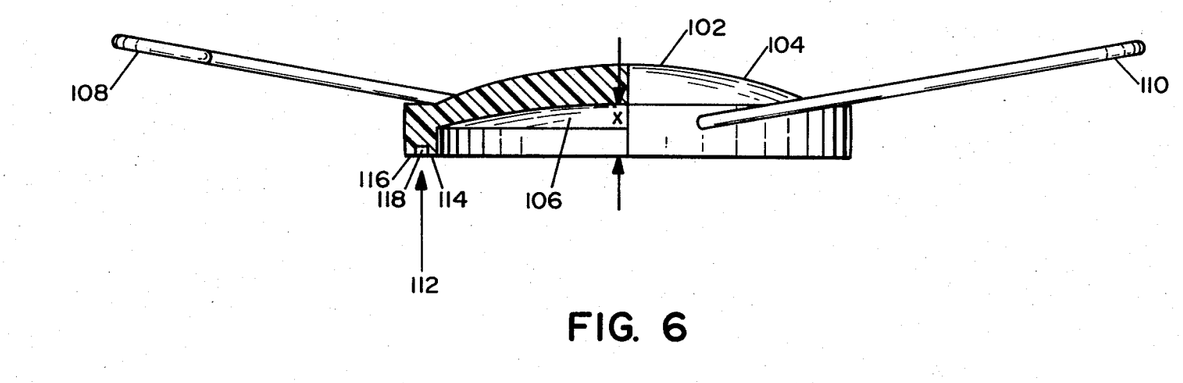
FIG. 6 illustrates a partial side view and a partial sectional view of FIG. 5.

FIG. 5 illustrates a plan view of an intraocular lens 100 including a lens optic 102 with anterior convex surface 104 and a posterior concave surface 106. Two loops 108 and 110 secure to the edge of the optic as previously described in FIGS. 1 and 2. A double barrier ledge 112, as also illustrated in FIG. 6, includes an inner ledge 114 and an outer ledge 116 separated by a channel 118. The ledge cross-section can be described as rectangular in nature, and affixing to the edge of the optic 102, where the ledge extends downwardly as illustrated in the figure. While in FIGS. 1–4 the concave posterior meniscus surface curves downwardly to meet the edge of the inner ledge, in FIGS. 5–8 the concave meniscus surface is offset away and upwardly from the inner edge of the inner ledge.

FIG. 6 illustrates a partial side view and a partial sectional view of FIG. 5 where all numerals correspond to those elements previously described. The ledge 116 is offset from the lens optic 102 by the width of the dual barriers and the channel in between at the plane of the end of each of the lens surfaces. The height of the cross-section of the ledge area is determined to provide sufficient spacing of the lens in the posterior chamber. An "x" in between the arrows illustrates nominal spacing of 0.3 mm between the posterior concave wall 106 of the optic 102 and a plane of the bottom of the optic 102.

Figure 7:
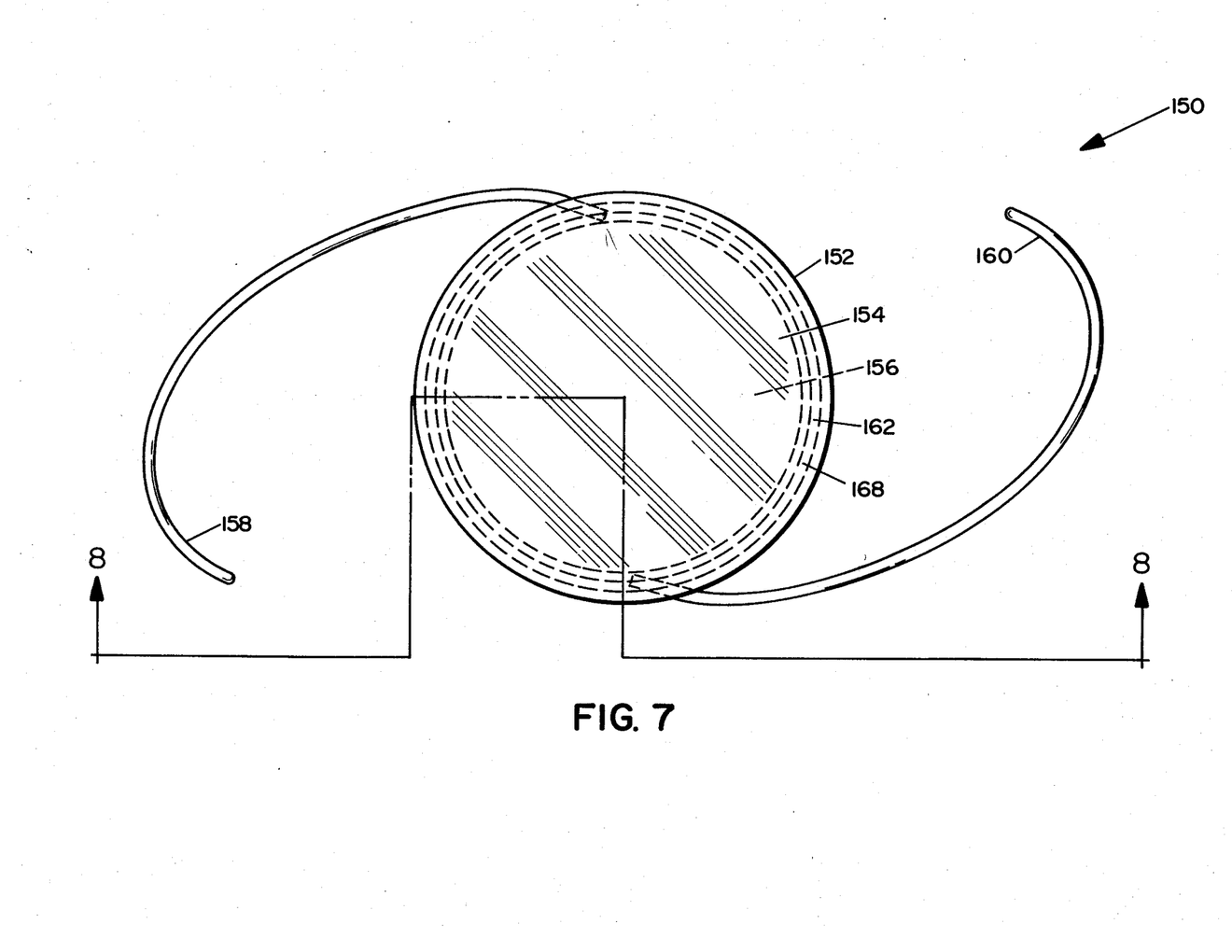
FIG. 7 illustrates a plan view of a lens.
Figure 8:
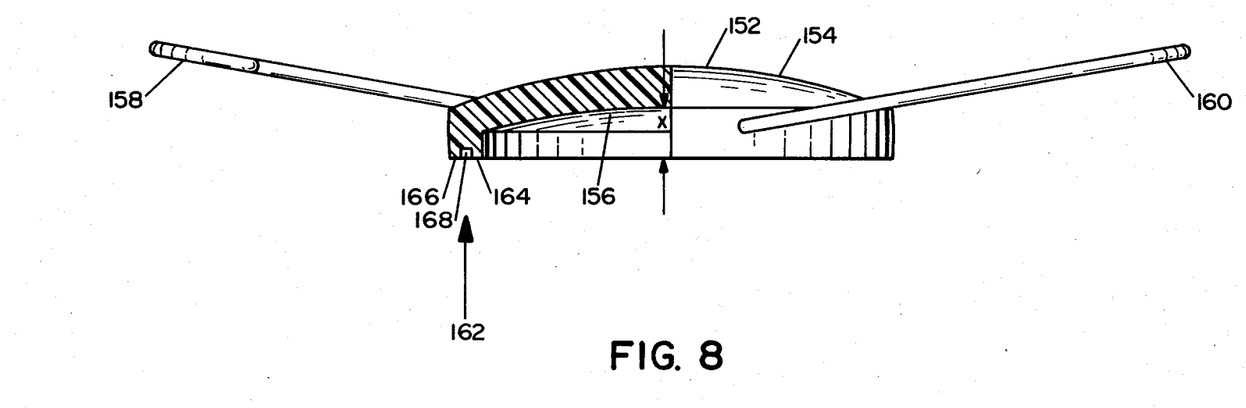
FIG. 8 illustrates a partial side view and a partial sectional view of FIG. 7.

FIG. 7 illustrates a plan view of an intraocular lens 150 including an optic 152 with an anterior convex surface 154 and a posterior concave surface 156. Two loops 158 and 160 secure to the edge of the optic as previously described in FIGS. 1 and 2. A double barrier ledge 162, as illustrated in FIG. 8, and includes an inner ledge 164 and an outer ledge 166 separated by a channel 168, where the entire structure extends downwardly from between the offset of the anterior curvature and the posterior curvature of the lens optic. This is also illustrated in FIG. 8.

FIG. 8 illustrates a partial side view and a partial sectional view of FIG. 7 where all numerals correspond to those elements previously described. It is illustrated in the figure that the ledge cross-section extends down between the edge of the anterior lens surface and the edge of the posterior lens surface of the lens optic. The height can be determined to provide sufficient spacing of the lens in the eye. An "x" in between the arrows illustrates nominal spacing of preferably 0.3 mm between the posterior concave wall 156 of the optic 152 and a plane of the bottom of the optic 152.

While the embodiments have illustrated a ledge cross-sectional area substantially rectangular, any ledge geometrical cross-sectional shape can be utilized, such as a rounded cross-section for supporting two rear ledge surfaces, or any other geometrical configuration. The rectangular cross-section has been submitted by way of example and for purposes of illustration only, and not to be construed as limiting of the present invention.

We claim:

1. Intraocular lens comprising:

a. lens optic including an anterior surface and a posterior surface;

b. plurality of loops secured into holes in said lens optic; and, c. multiple barrier channeled ledge extending about said optic surfaces, and including a plurality of downwardly extending ledges having a channel therebetween which ledges extend in a posterior direction away from said posterior surface so as to space said posterior lens surface away from the posterior capsule while forming a double seal therewith when engaged with the posterior capsule.

2. Lens of claim 1 wherein said ledge comprises an upper ledge and a lower ledge, said upper ledge being longer in land surface to said lower ledge.

3. Lens of claim 1 wherein said ledge comprises an upper ledge and a lower ledge, said upper ledge being equal in land surface to said lower ledge.

4. Lens of claim 1 wherein said ledge comprises an upper ledge and a lower ledge, said upper ledge being shorter in land surface to said lower ledge.

5. Lens of claim 1 wherein said channel is U-shaped.

6. Lens of claim 1 wherein said channel is a predetermined geometrical configuration.

7. Lens of claim 1 wherein said ledge extends downwardly from said lens optic.

8. Lens of claim 1 wherein said ledge is between an edge of said optic and said posterior surface.

9. Lens of claim 1 wherein said multiple barriers comprise two with a channel therebetween.

10. Lens of claim 1 wherein said posterior surface is concave.

11. Lens of claim 1 wherein said posterior surface is plano.

* * * * *